United States Patent
Miyashita et al.

[11] Patent Number: 5,724,531
[45] Date of Patent: Mar. 3, 1998

[54] METHOD AND APPARATUS OF MANIPULATING AN OBJECT ON A DISPLAY

[75] Inventors: Shichiro Miyashita, Yamato; Toru Tachibana, Yokohama; Yuhgoh Tanabe, Tokyo-to, all of Japan

[73] Assignee: International Business Machine Corp., Armonk, N.Y.

[21] Appl. No.: 681,341

[22] Filed: Jul. 22, 1996

[30] Foreign Application Priority Data

Jul. 28, 1995 [JP] Japan ................. 7-193669

[51] Int. Cl.$^6$ ................. G06F 3/14
[52] U.S. Cl. ................. 395/339; 395/354; 345/145
[58] Field of Search ................. 395/339, 354, 395/326, 358, 348, 349, 977, 973; 345/145, 146, 157, 156

[56] References Cited

U.S. PATENT DOCUMENTS

| | | | |
|---|---|---|---|
| 4,698,625 | 10/1987 | McCaskill et al. | 345/157 |
| 5,307,457 | 4/1994 | Beitel et al. | 395/348 |
| 5,363,481 | 11/1994 | Tilt | 395/973 X |
| 5,428,734 | 6/1995 | Haynes et al. | 395/349 |
| 5,436,637 | 7/1995 | Gayraud et al. | 395/348 X |
| 5,450,539 | 9/1995 | Ruben | 395/354 |
| 5,546,521 | 8/1996 | Martinez | 395/348 X |
| 5,565,888 | 10/1996 | Selker | 345/146 |
| 5,583,984 | 12/1996 | Conrad et al. | 395/348 X |

*Primary Examiner*—Raymond J. Bayerl
*Attorney, Agent, or Firm*—A. Bruce Clay

[57] ABSTRACT

A GUI permits an object to be selected without using a click button, and can be easily operated with few erroneous operations. When a user wants to select an upper scroll button 20, the user brings a pointer 32 in contact with the button 20. When the pointer 32 is moved (step 120) and contacts the scroll button 20 (step 140), the scroll button 20 is reduced by four dots toward the frame side, and the movable range of the pointer 32 is increased by four dots (step 150). The user continues to move the pointer 32 to the scroll button 20 side (step 170). When the pointer 32 contacts the scroll button 20 again (step 190), the scroll button 20 is reduced by four dots, and the movable range of the pointer 32 is increased by four dots again (150). This operation is repeated. Finally, when a count has exceeded a specific value, 3 (step 210), a depression event for the scroll button 20 is transmitted to an application program (step 220), which in turn performs scrolling of the display area (step 230).

12 Claims, 7 Drawing Sheets

METHOD AND APPARATUS OF MANIPULATING AN OBJECT ON A DISPLAY

FIELD OF THE INVENTION

The present invention relates in general to a data processing system; and more specifically, to a method and apparatus for selecting an object without using a click button in a design for a graphic user interface (GUI).

BACKGROUND OF THE INVENTION

Conventionally, a GUI, such as Windows or OS/2 Workplace Shell, is designed with the premise that a screen size is at least 7 inches, and the common operation is to click a button on a screen for selecting an object. For a palmtop PC that has a screen of less than 5 inches, this operation is not easily performed for the following reasons:

1. Icons, buttons and pointers are all small, so that it is difficult to position a pointer at a target location. In Windows and OS/2 Workplace Shell, scroll buttons and enlarging/reducing buttons especially are too small to handle.
2. Basically, an operation cannot be performed with a single finger. The selection of an object by clicking a button is difficult while a PC is supported in one hand and a pointer has to be controlled at the same time.

Double clicking is normally required to select an object on a sufficiently large common screen. This operation, however, requires a certain degree of skill, and is difficult for a beginner. Further, double clicking is a barrier to the use of computers for those handicapped individuals whose condition does not permit the full use of their hands or fingers.

As is described in "Lotus Super Office Guide", p.21, August 1994, by Lotus Development Corporation (Lotus is a trademark of Lotus Development Corporation), there is a technique (bubble Help) by which when a mouse pointer is located on a Smart Icon (Smart Icon is a trademark of Lotus Development Corporation), a bubble is displayed in which an explanation for the icon is given. However, since if it were possible to select objects merely by placing a pointer on the object, erroneous operations would tend to occur and thus it would be very difficult to operate the GUI. Therefore, only an explanation for the icon is displayed, and it is not possible to provide a GUI that permits an object to be selected without using a click button and that is easily employed with fewer erroneous operations.

It is one object of the present invention to provide a processing system that can easily perform the selection of an object even on a display screen of an insufficient size, and that can perform the object selection while the data processing system, such as a palmtop PC, is supported with one hand. It is another object of the present invention to provide a computer system with an object selection means that even a beginner can operate easily on a normally sized, sufficiently large screen, and that can be easily operated by handicapped users who do not have full use of their hands or fingers. It is an additional object of the present invention to provide a processing system that permits an object to be selected without using a click button, and that can be provided a GUI that is easily operated with few erroneous operations. It is a further object of the present invention to provide a more compactly made portable PC that enables a pointing device to control a pointer and that does not employ a click button as a requisite component.

SUMMARY OF THE INVENTION

A method, according to the present invention, by which a pointing device controls a pointer to perform an operation with an object that is located adjacent to one side of a frame of a window on a display screen and that is displayed on the screen, comprises: (a) a step of excluding from a movable range for the pointer a neighborhood of a display area for the object; (b) a step of detecting a movement of the pointer; (c) a step of determining that the pointer is located in the neighborhood of the display area for the object when the movement is detected at the step (b); (d) a step of reducing the display area of the object when it is determined at the step (c) that the pointer is located in the neighborhood; (e) a step of enlarging the movable range, by a value that is equivalent to the display area of the object that is reduced at the step (d), when the pointer is determined at the step (c) to be located in the neighborhood; (f) a step of repeating the steps (b) through (e); (g) a step of counting a number of repetitions at the step (f); (h) a step of determining when a count acquired at the step (g) reaches a first value; (I) a step of, when at the step (h) the count reaches the first value, transmitting to an application program a notification of a selection event for the object; (j) a step of performing a process by the application program in consonance with a type of the object; (k) a step of determining that the pointer is located outside of an area in the neighborhood of the original display area for the object at the step (a); and (l) a step of, when at the step (k) the pointer is located outside of the area, returning the display area for the object to an original size for the display area of the object at the step (a).

The object can serve as a screen scroll button or a function button.

The step for reducing the display area of the object can include a step of reducing the object by a desired number of dots along a line that is parallel to the frame of the window.

The object can be formed so that it has the shape of an isosceles trapezoid.

A method of the present invention, after it is determined that the count reaches the first value, further comprises: (f2) a step for repeating the steps (b) through (e); (g2) a step for counting a number of repetitions at the (f2); (h2) a step of determining that a count acquired at the step (g2) reaches a second value; (i2) a step of transmitting to an application a notification of a second event, which relates to the object, when the count reaches the second value at the step (h2); and (j) a step of performing a process by the application program that is in consonance with the second event.

A method of the present invention further comprises: (i3-1) a step of measuring a period of time during which the count is maintained at the first value at the step (h); and (i3-2) a step of, when the period measured at the step (i3-1) reaches a specific time, transmitting to an application program a notification of a selection event for the object.

A method of the present invention further comprises a step of restricting the movement of the pointer in a direction that is parallel to one side of the frame of the window within an enlarged movable range.

According to another aspect of the present invention, a method, by which an object displayed on a screen is operated by using a pointer that is controlled by a pointing device, comprises: (a) a step of excluding a neighborhood of a display area for the object from a movable range for the pointer; (b) a step of detecting a movement of the pointer; (c) a step of determining that the pointer is located in the neighborhood of the display area for the object; (d) a step of measuring a period of time during which the pointer is located in the neighborhood at the step (c); and (e) a step of, when the period measured at the step (d) reaches a specific time, transmitting to an application program a notification of a selection event for the object.

According to an additional aspect of the present invention, a method, by which an object displayed on a screen is operated by using a pointer that is controlled by a pointing device, comprises: (a) a step of excluding from a movable range for the pointer a neighborhood of a display area for the object; (b) a step of detecting a movement of the pointer; (c) a step of determining that the pointer is located in the neighborhood of the display area for the object; (d) a step of changing the display area of the object when it is determined at the step (c) that the pointer is located in the neighborhood; and (e) a step of, when it is determined at the step (c) that the pointer is located in the neighborhood, transmitting to an application program a notification of a selection event for the object.

An apparatus of the present invention, for operating an object displayed on a screen, comprises: (a) means for excluding a neighborhood of a display area for the object from a movable range for the pointer; (b) means for detecting a movement of the pointer; (c) means for determining that the pointer is located in the neighborhood of the display area for the object; (d) means for changing the display area for the object when it is determined by the means (c) that the pointer is located in the neighborhood; and (e) means for, when it is determined by the means (c) that the pointer is located in the neighborhood, transmitting to an application program a notification of a selection event for the object.

According to another aspect of the present invention, an apparatus, which incorporates an LCD device, memory and a CPU in a portable housing case, and which employs a pointer that is controlled by a pointing device to manipulate an object that is located adjacent to one side of an frame of a window on a screen of the LCD device and that is displayed on the screen, comprises: (a) means for excluding a neighborhood of a display area for the object from a movable range for the pointer; (b) means for detecting a movement of the pointer by the pointing device; (c) means for determining that the pointer is located in the neighborhood of the display area for the object when the movement is detected by the means (b); (d) means for reducing the display area for the object when it is determined by the means (c) that the pointer is located in the neighborhood; (e) means for enlarging the movable range, by a value that is equivalent to the display area of the object that is reduced by the means (d), when the pointer is determined by the means (c) to be located in the neighborhood; (f) means for performing multiple iterations of operations that are performed by the means (b) through (e); (g) means for counting a number of repetitions by the means (f); (h) means for determining when a count acquired by the means (g) attains a first value; (i) means for, when the means (h) determines that the count attains the first value, transmitting to an application program a notification of a selection event for the object; (j) means for performing a process by the application program in consonance with a type of the object; (k) means for determining that the pointer is located outside of an area in the neighborhood of the original display area for the object before operation of the means (a); and (l) means for, when the means (k) determines that the pointer is located outside of the area, returning the display area for the object to an original size for the display area of the object at the means (a).

BRIEF DESCRIPTION OF THE DRAWINGS

For a more complete understanding of the present invention and for further advantages thereof, reference is now made to the following Detailed Description taken in conjunction with the accompanying drawings in which.

DETAILED DESCRIPTION OF THE INVENTION

Figure 1:
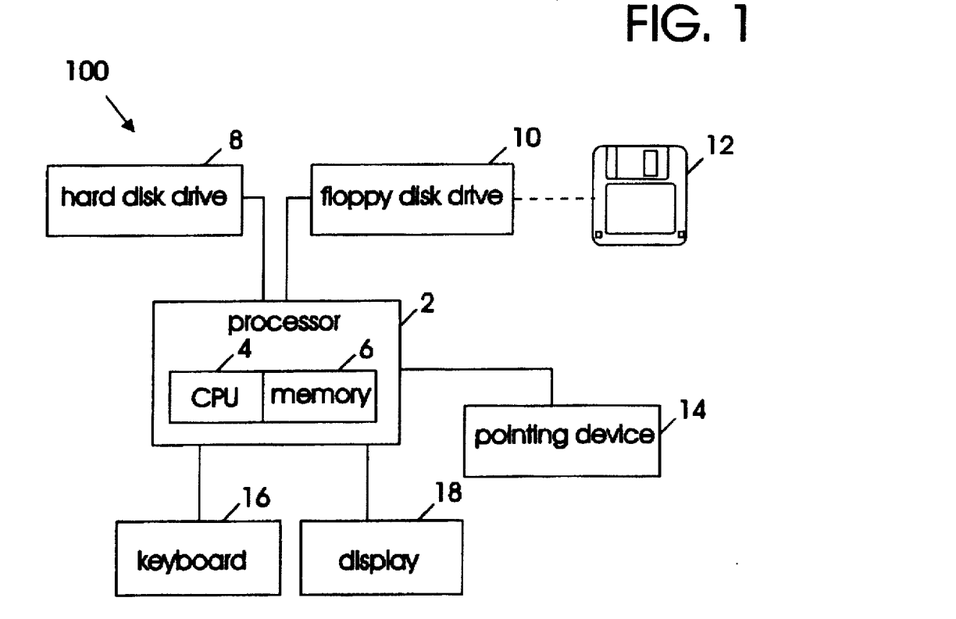
FIG. 1 is a block diagram illustrating a data processing system that is a part of an apparatus of the present invention for the performance of the method of the present invention.

FIG. 1 is a block diagram illustrating a data processing system 100 according to the present invention. The data processing system 100 comprises a processor 2, which includes a central processing unit (CPU) 4 and a memory 6. To the processor 2 are connected a hard disk drive 8 and a floppy disk drive 10, which serve as auxiliary storage devices. Into the floppy disk drive 10 is inserted a diskette 12, on which is recorded code of a computer program to carry out the present invention using the data processing system 100. The data processing system 100 can also include user interface hardware, such as a pointing device 14 or a keyboard 16, for input data to the processor 2, and a display 18 for displaying data to a user. The pointing device 14 is, for example, a mouse, a track ball, a Track Point (trademark of IBM Corp.), or a joy stick.

Figure 2:
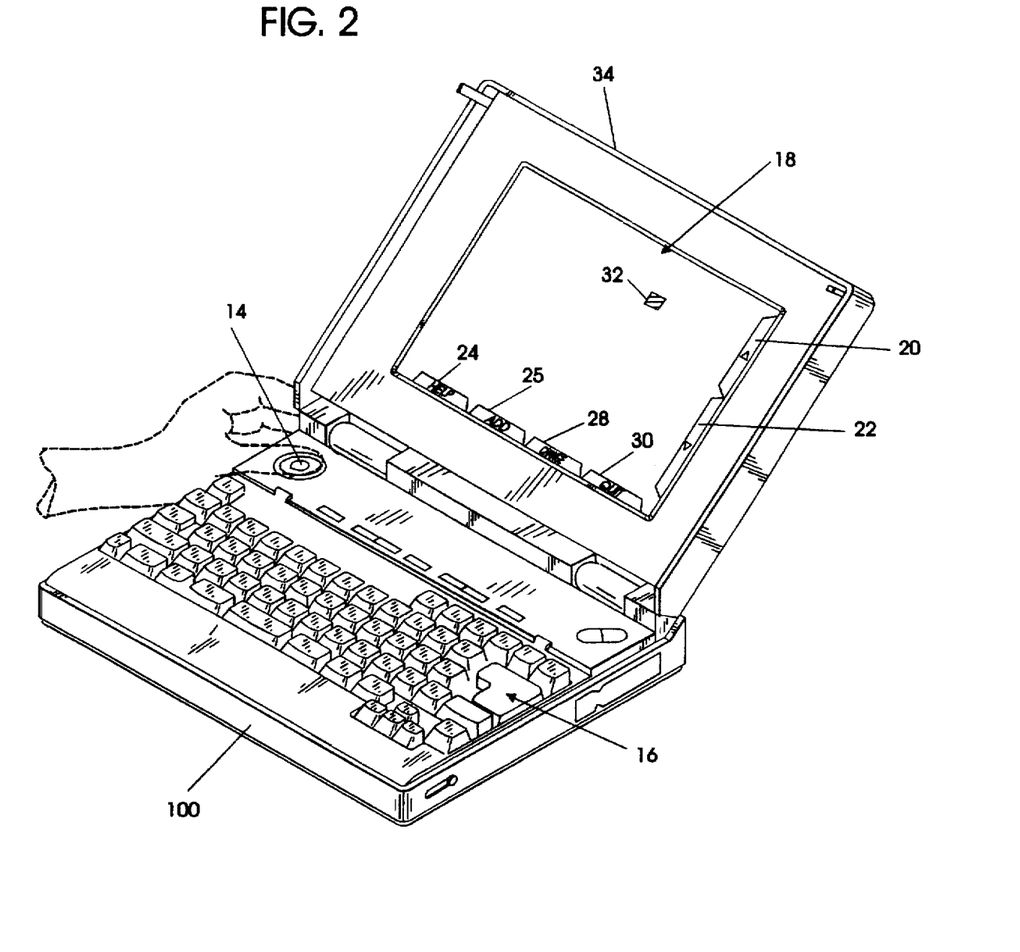
FIG. 2 is a diagram illustrating the entire frame appearance of an apparatus according to one preferred embodiment of the present invention.

FIG. 2 is a diagram illustrating the frame appearance of one preferred embodiment of the data processing system 100 of the present invention. The present invention is applied to a palmtop PC that is so small that it can be supported in a person's palm, as is shown in FIG. 2. The palmtop PC is supported by only a single hand, and a pointing device 14 can be operated by a single thumb. According to the present invention, in this manner the selection of an object can be easily performed by a single finger.

Figure 3:
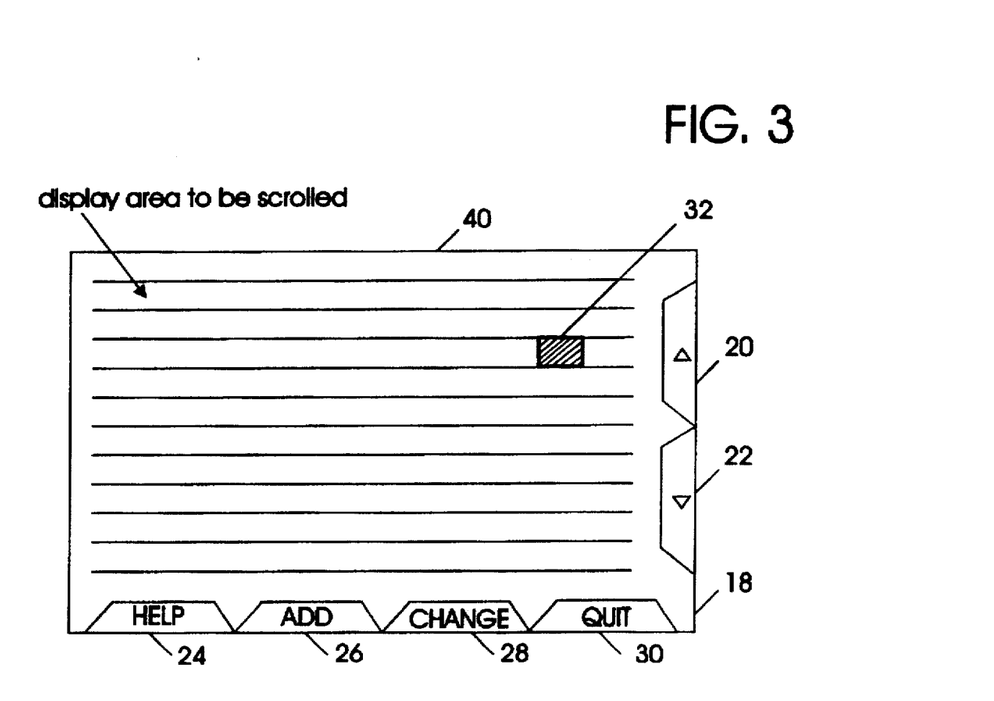
FIG. 3 is a diagram illustrating a display screen for the apparatus according to the preferred embodiment of the present invention.

FIG. 3 is an enlarged diagram showing a display screen 18 of the palmtop PC 100 in FIG. 2. Although only a single window is shown to simplify the explanation, it would be obvious to one having ordinary skill in the art that the present invention can be employed to display multiple windows. FIG. 3 shows a screen frame 40 and a display area which can be scrolled in the center of the display screen 18. Scroll buttons 20 and 22 are located adjacent to the right side of the screen frame 40, and function buttons 24, 26, 28 and 30 are located adjacent to the bottom of the screen frame 40. The scroll buttons 20 and 22 and the function buttons 24, 26, 28 and 30 that are displayed are shaped like isosceles trapezoids. The buttons, however, can take another shape, such as a semicircle, an oblong, or a rectangle, and can be located in the center of the display screen 18 and not adjacent to the screen frame 40. The function buttons 24, 26, 28 and 30 can also serve as PF keys. In addition, the selection of a PF key can be performed after a movement key or a control key is chosen. A pointer 32 can freely move within the display screen 18 excluding the positions occupied by the scroll buttons 20 and 22 and the function buttons 24, 26, 28 and 30.

Figures 4, 4B:
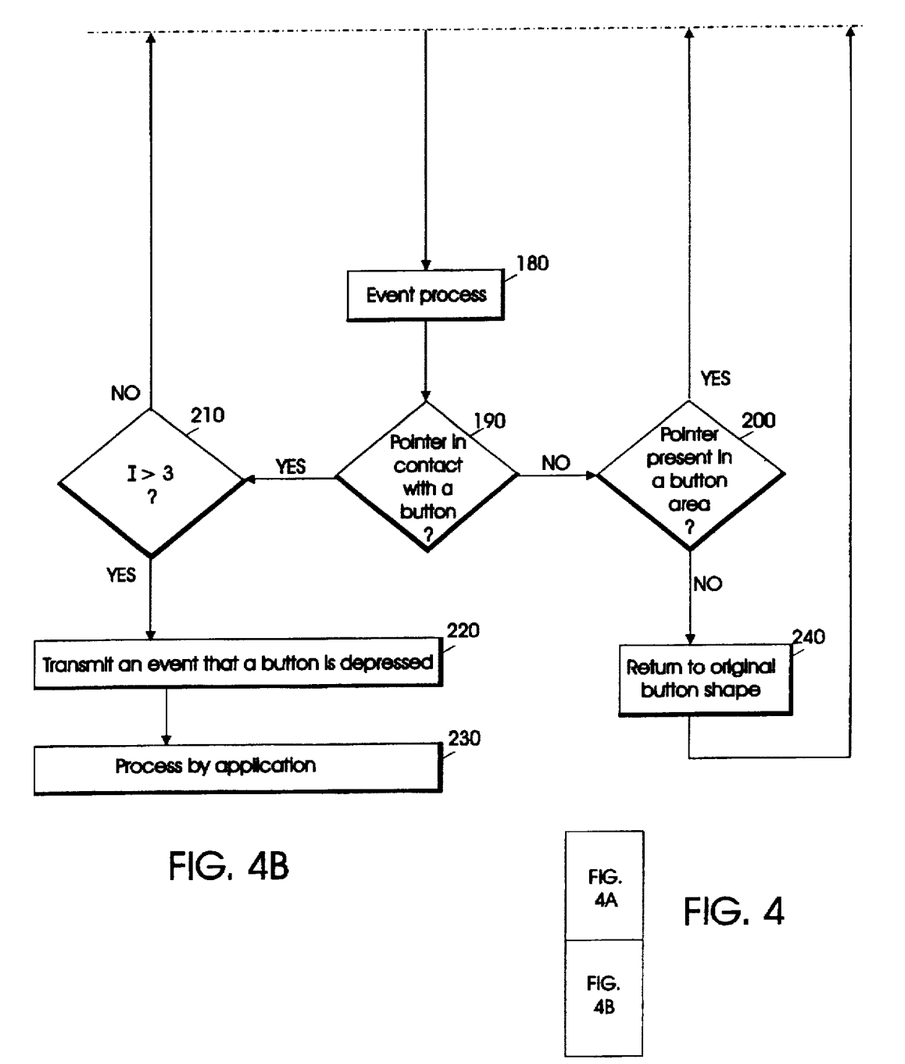
FIGS. 4, 4A and 4B comprise a flowchart showing processing for the preferred embodiment of the present invention.
Figure 4A:
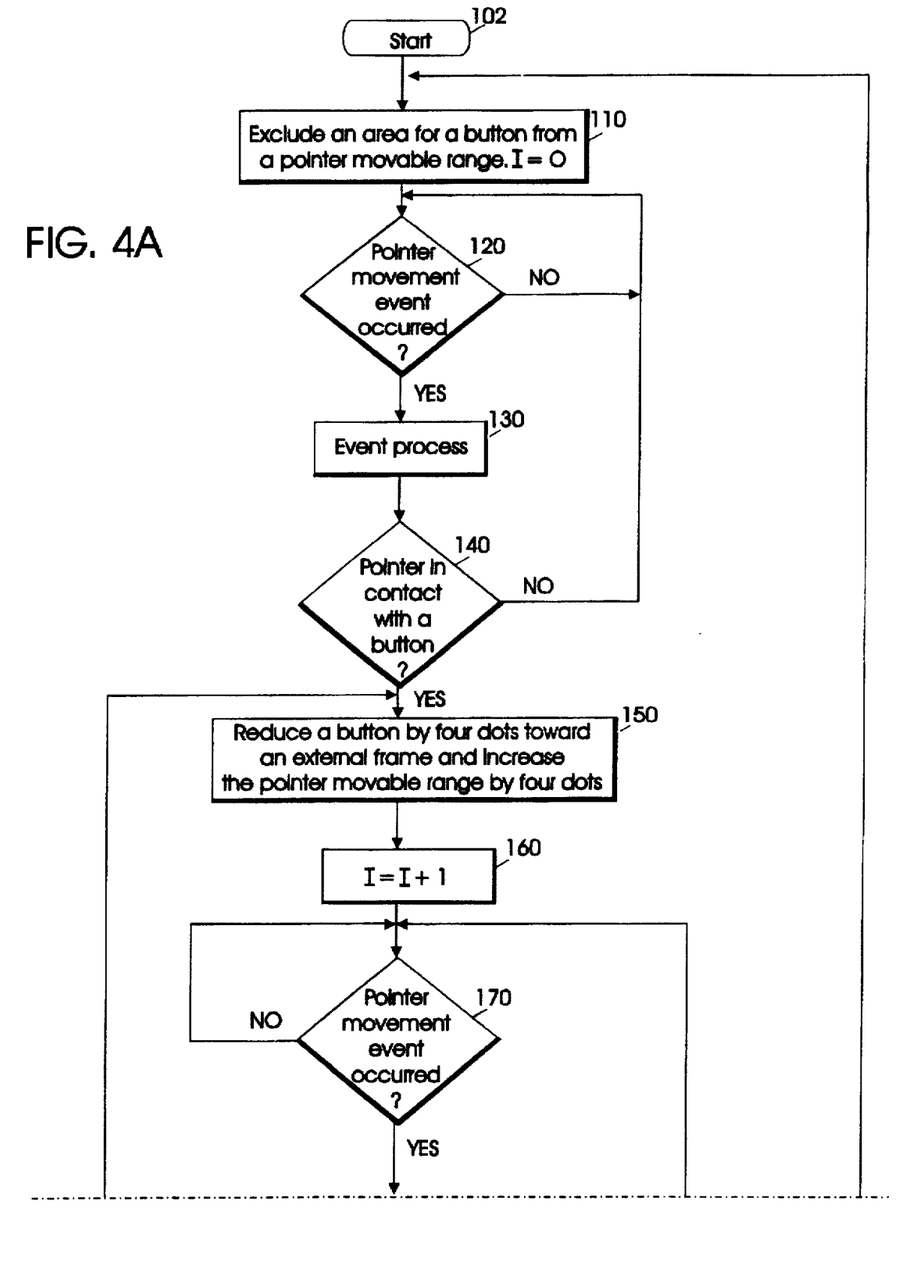

FIGS. 4A and 4B comprise a flowchart showing the processing of the present invention. At process block 110, the areas occupied by the buttons are excluded from a range 36 (see FIG. 13) wherein the pointer 32 can move. At this time, a counter (I) holds a value "0". Program control then waits until an event occurs at the pointer 32. When, at decision block 120, the moving of the pointer 32 is detected, at process block 130, processing for the event, i.e, a process for moving the pointer 32 in the movable range 36, is performed. Then, at process block 140, a check is performed to determine whether or not the pointer 32 is in contact with the button 20. When the pointer 32 is in contact with the button 20, at process block 150, the button 20 is reduced by four dots toward the frame side, so that the movable range 36 for the pointer 32 is increased by four dots. At process block 160, a value held by a counter is incremented by "1". Then, program control waits for an occurrence of a movement event at the pointer 32. When, at decision block 170, the moving of the pointer 32 is detected, at process block 180, a process for the event is performed.

Figure 11:
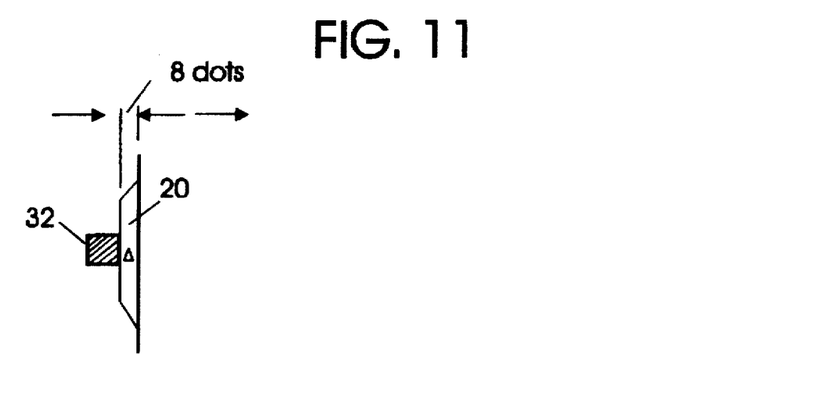
FIG. 11 is a diagram showing the pointer and a change in the scroll button according to the preferred embodiment of the present invention.

At process block 190 a check is performed to determine whether or not the pointer 32 is in contact with the button 20. When the pointer 32 is not in contact with the button 20, at decision block 200 a check is performed to determine whether or not the pointer 32 exists in the original area of the button 20 shown in FIG. 5. When the pointer 32 exists in that area, it is assumed that the selection of an object is being performed, and program control again waits for the movement of the pointer 32. When the pointer 32 is outside of the area of the button 20, it is assumed that the selection of an object is halted. At process block 240, the area of the button 20 is increased to its original size, as is shown in FIG. 11.

If, at decision block 190, the pointer 32 is in contact with the button 20, at decision block 210 a check is performed to determine whether or not the value held by the counter has exceeded a predetermined number (3). When the value held by the counter does not exceed the predetermined number, it is assumed that the selection of an object is being performed. At process block 150, the button 20 is reduced again by four dots to the frame side, and the movable range 36 for the pointer 32 is increased by four dots. If, at decision block 210, the value held by the counter has exceeded the predetermined number, it is assumed that the selection of an object is completed, and at process block 220, a notification of the button 20 selection event is transmitted to an application program. At process block 230, the application program executes an operation that corresponds to a selected object. Since the present invention can be achieved through the above described processing, alteration of a conventional mouse driver is not required, and all the conventional devices that control the mouse pointer can be supported. Further, in the present invention, since as is shown in the flowchart the selection of an object (the button 20) can be performed by only moving the pointer 32 while using the pointing device 14, a portable PC that does not require a click button can be provided.

An explanation will now be given, while referring to FIGS. 5 through 11, of how the processing for the preferred embodiment of the invention is displayed on the display screen. First, a user must select the upper scroll button 20 of the screen to scroll up a currently displayed area. The user uses the pointing device 14 and moves the pointer 32 to the position shown in FIG. 5. The pointer 32 can be replaced by a cursor that is controlled at the keyboard 16. The pointer 32 does not necessarily need to be moved to the center of the scroll button 20, and may contact any left side portion of the scroll button 20. The decision whether or not the pointer 32 is in contact with the displayed scroll button 20 can be replaced with a decision whether or not the pointer 32 exists in an area, in the predetermined neighborhood of the scroll button 20. Especially when the scroll button 20 is displayed in three dimensions, the pointer 32 moving into the displayed area of the scroll button 20 can more clearly appeal that an image depicting the pointer 32 is contacting with the scroll button 20 to users.

Figure 6:
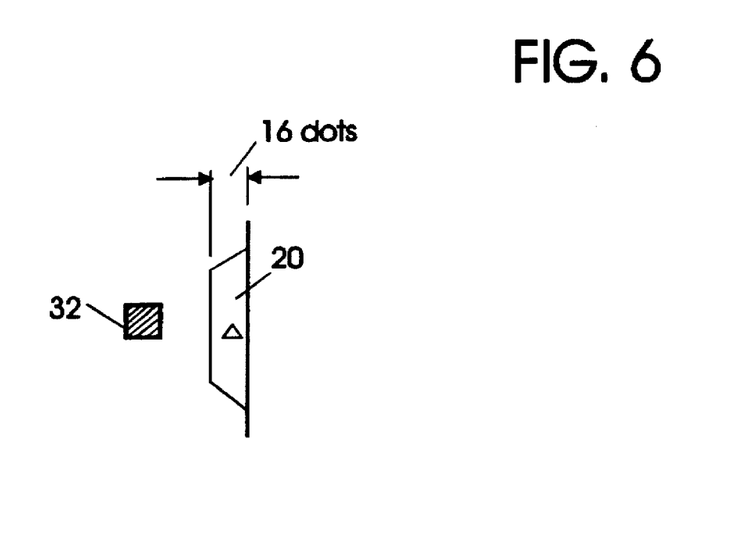
FIG. 6 is a diagram showing the pointer and a change in the scroll button according to the preferred embodiment of the present invention.

As is described by referring to FIG. 4, when the pointer 32 is moved and contacts the scroll button 20, the scroll pointer 20 is reduced by four dots toward the frame side, and the movable range 36 of the pointer 32 is increased by four dots (see FIG. 6). Although, in this embodiment, the area of the scroll button 20 is reduced by four dots, a reduction by one dot is also possible. Further, a user can set a value for reduction, or the value can be controlled by using a value held by the counter. In addition, the number of dots to be reduced and the number of dots to be increased can be set by users as different values. In this case, the procedure at decision block 190 in FIG. 4 should be changed to enable a determination of whether or not the pointer 32 is at the limit of the movable range.

Figure 7:
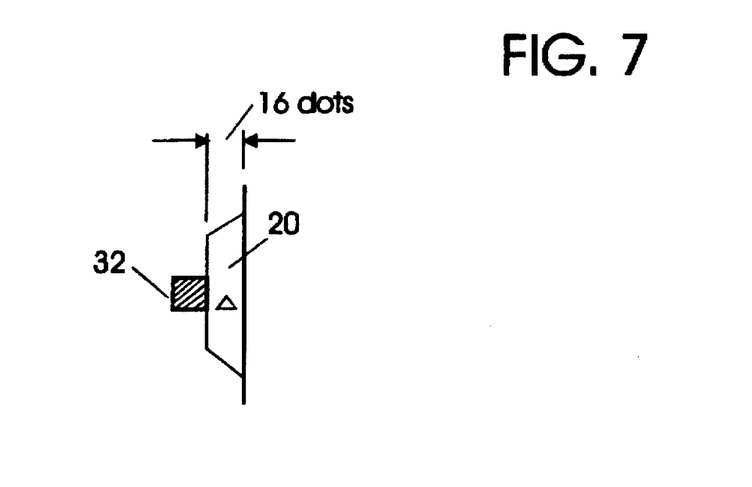
FIG. 7 is a diagram showing the pointer and a change in the scroll button according to the preferred embodiment of the present invention.
Figure 8:
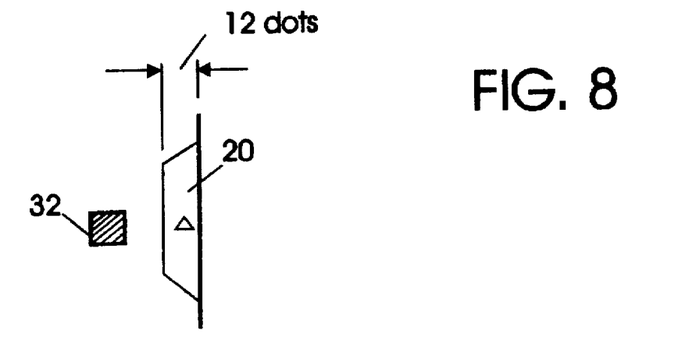
FIG. 8 is a diagram showing the pointer and a change in the scroll button according to the preferred embodiment of the present invention.
Figure 9:
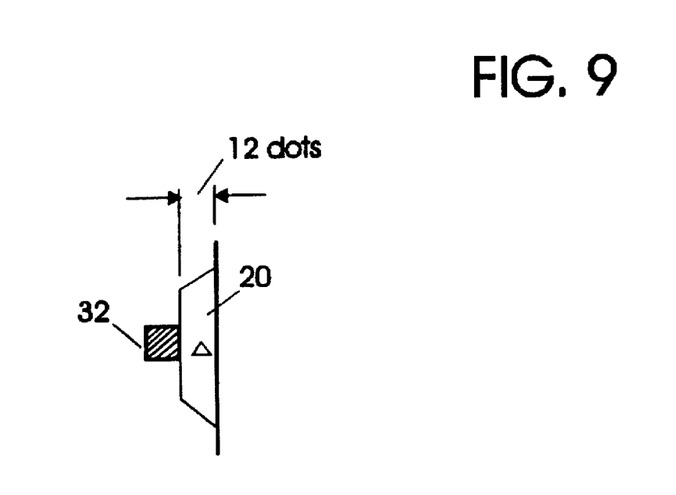
FIG. 9 is a diagram showing the pointer and a change in the scroll button according to the preferred embodiment of the present invention.
Figure 10:
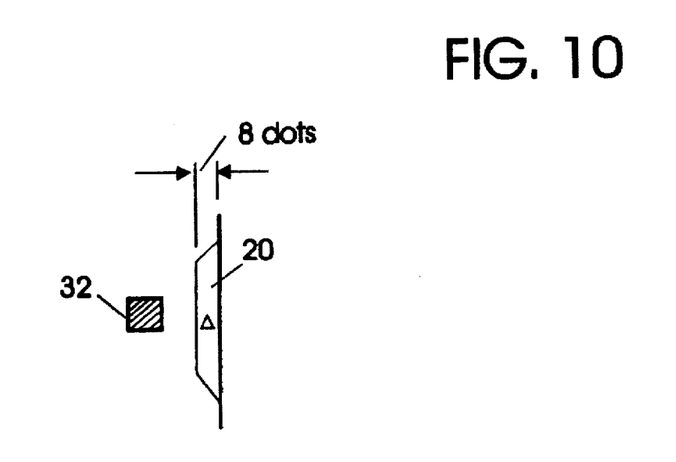
FIG. 10 is a diagram showing the pointer and a change in the scroll button according to the preferred embodiment of the present invention.

In FIG. 6, the area of the scroll button 20 is reduced by four dots, and a user continues to move the pointer 32 to the right. When the pointer 32 contacts the scroll button 20 again (see FIG. 7), the scroll button 20 is reduced by four dots toward the frame side, and the movable range 36 of the pointer 32 is increased by four dots (FIG. 8). This operation is repeated (FIGS. 9 and 10). Finally, when, as is shown in FIG. 11, the pointer 32 contacts the scroll button 20, a value held by the counter has exceeded a specific value, 3, and a depression event for the scroll button 20 is transmitted to an application program, which in turn performs scrolling of the display area. In this case, in order to notify a user that the scroll button 20 has been selected, a means that employs a sound effect to alert a user, or that changes the color or the luminance of a selected scroll button 20, is effective. A specific value can also be set by a user.

For the transmission to an application program of a selection event for the scroll button 20, an operation for reducing the area of the scroll button 20 by a predetermined number of dots toward the frame, and for increasing the movable range 36 of the pointer 32 by a predetermined number of dots, is repeated to finally bring the pointer 32 into contact with the scroll button 20, and whether or not a counter value has exceeded a specific value is determined. The operation for the determination can be replaced with an operation for transmitting to the application program a selection event for the scroll button 20 under the following conditions: if, in FIG. 7, the operation for reducing the scroll button 20 by a predetermined number of dots toward the frame and for enlarging the movable range 36 of the pointer 32 by a predetermined number of dots is not performed; and when a period where the condition in FIG. 7 is continued is measured and is found to be longer than a preset period (which a user can also set). Instead of the period of time, the strength of the force that is applied to the pointing device (e.g., a resistance value for a track point) can be measured and can be employed as a determination reference.

When the pointer 32 contacts the scroll button 20 in FIG. 11, the counter value has exceeded a specific value, so that a selection event for the scroll button 20 is transmitted to the application program, which in turn performs scrolling of the display area. In addition to this process, if a count of the number of seconds the condition in FIG. 11 continues is made and the result is equal to or greater than a preset time value, an event that is different from the previous event can be transmitted to the application program. For example, upon receipt of the first event, the application program may scroll the display screen by one line, while upon receipt of the second event, the application program may perform fast scrolling of a plurality of lines (e.g., by page).

To generate the event (the second event) that is different from the previous event, after the previous event (the first event) has occurred, an operation is repeated according to which the scroll button 20 is reduced by a greater given number of dots toward the frame so that the movable range 36 of the pointer 32 is increased by the given number of dots, the pointer 32 finally contacts the scroll button 20, and the counter value is greater than the second specific value.

The process performed by the application program can be terminated when the state in FIG. 11, where the pointer 32 is in contact with the scroll button 20, is released. The decision to release the pointer 32 from the scroll button 20, can substitute for the pointer 32 in FIG. 11 to be separated from the scroll button 20 by an expected number of dots, for the pointer 32 to be located away from the original area of the scroll button 20 before it is reduced, and for a scroll halt button to have been selected. When a PF key and a movement key, or a control key, are employed as function buttons, a combination of the movement key and the PF 5 key is established by selecting the shift key and then the PF 5 key. The release of the shift key should be performed when the movement of the pointer 32 away from the PF 5 key occurs before reduction, or when a selection halt button is selected.

Figure 5:
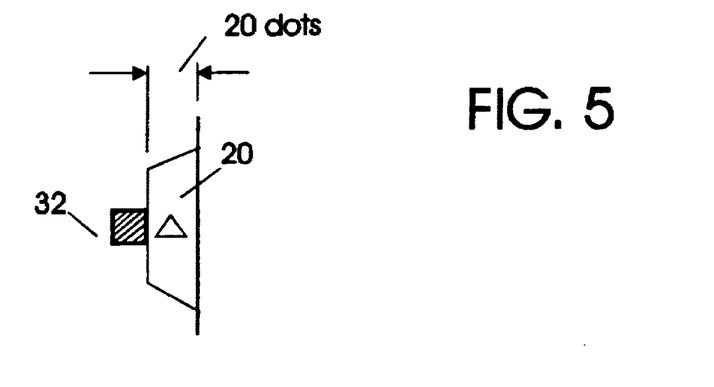
FIG. 5 is a diagram showing a pointer and a change in a scroll button according to the preferred embodiment of the present invention.
Figure 12:
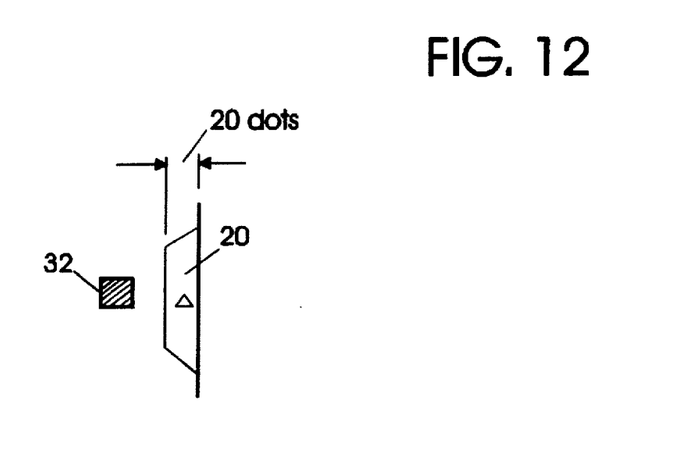
FIG. 12 is a diagram showing the pointer and a change in the scroll button according to the preferred embodiment of the present invention.

When the pointer 32 is located away from the range the equivalent of the original area of the scroll button 20 in FIG. 5, or when the scroll halt button is selected, the scroll button 20 can be returned to its original size, as is shown in FIG. 12.

Figure 13:
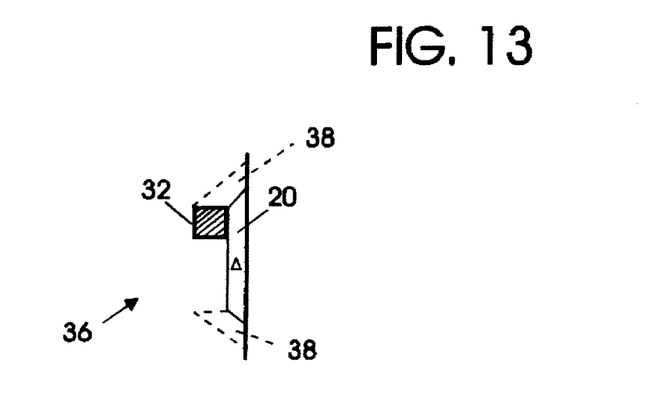
FIG. 13 is a diagram showing a pointer provided according to and a range within which the movement of the pointer is inhibited an additional function of the present invention.

As an additional function, the present invention has means for restricting the movement of the pointer 32 in a specific direction within an enlarged movable range. This function can be provided, as is shown in FIG. 13, by simply enlarging the movable range 36 perpendicular to the upper side of the isosceles trapezoid and by defining the other areas as movement inhibiting ranges 38. The additional function of the present invention can prevent erroneous operations such as the unexpected interruption of the objection selection and the erroneous selection of another object adjacent to a desired object.

As is described above, according to the present invention, selection of an object can be easily performed even on a small display screen. Further, while a palmtop PC is supported by one hand, the selection of an object can be performed with the PC. Object selection means that even a beginner can easily operate can be provided for a normal, sufficiently large screen. A computer system can be provided that people with limited use of their hands or fingers can easily operate. An easily operated GUI can be provided, by which an object can be selected without using a click button and with which erroneous operations seldom occur. A smaller portable PC can be provided that has a pointer that can be controlled by a pointing device, and for which a click button is not a requisite component.

Although the present invention has been described with respect to a specific preferred embodiment thereof, various changes and modifications may be suggested to one skilled in the art, and it is intended that the present invention encompass such changes and modifications as fall within the scope of the appended claims.

We claim:

1. A method for operating an object which is displayed on a display screen located adjacent to one side of a frame of a window on said display screen by using a pointer displayed on said display screen and controlled by a pointing device, comprising the steps of:
    (a) excluding a neighborhood of a display area for said object from a movable range for said pointer;
    (b) detecting a movement of said pointer;
    (c) determining that said pointer is located in said neighborhood when said movement is detected at said step (b);
    (d) reducing said display area for said object when it is determined that said pointer is located in said neighborhood at said step (c);
    (e) enlarging said movable range according to said display area for said object that is reduced at said step (d), when said pointer is determined at said step (c) to locate in said neighborhood;
    (f) repeating said steps (b) through (e);
    (g) counting a number of repetitions of said step (f);
    (h) determining when a count at said step (g) reaches a predetermined first value;
    (i) transmitting an event indicating a selection of said object to an application program;
    (j) performing a process by said application program corresponding to a type of said object;
    (k) determining that said pointer is located outside of said neighborhood at said step (a); and
    (l) restoring said display area for said object to an original size of said display area of said object when at said step (k) said pointer is located outside of said area.

2. The method according to claim 1, wherein said object is a screen scroll button.

3. The method according to claim 1, wherein said step (d) for reducing said display area of said object further comprises a step of reducing said object by a desired number of n dots in which n is a natural number along said frame of said window.

4. The method according to claim 1, wherein said object has the shape of an isosceles trapezoid.

5. The method according to claim 1, after it is determined at said step (h) that said count has reached said first value, further comprising the steps of:

(f2) repeating said steps (b) through (e);

(g2) counting a number of repetitions at said step (f2);

(h2) determining that a count reaches a second value at said step (g2);

(i2) transmitting a second event which related to said object to an application, when said count reaches said second value at said step (h2); and (j2) performing a process by said application program corresponding to said second event.

6. The method according to claim 1, after it is determined at said step (h) that said count has reached said first value, further comprising the steps of:

(i3-1) measuring a period of time during which said count is maintained at said first value at said step (h);

(i3-2), transmitting an event indicating a selection of said object to an application program, when said period measured at said step (i3-1) reaches a specific time; and (j) performing a process by said application program corresponding to said second event.

7. The method according to claim 1, further comprising a step of restricting a movement of said pointer in a direction that is parallel to one side of said frame of said window within a movable range that is enlarged at said step (e).

8. A method for operating an object displayed on a screen by using a pointer displayed on said screen and controlled by a pointing device, comprising the steps of:

(a) excluding a neighborhood of a display area for said object from a movable range for said pointer;

(b) detecting a movement of said pointer;

(c) determining that said pointer is located in said neighborhood;

(d) measuring a period of time during which said pointer is located in said neighborhood at said step (c); and (e) transmitting an event indicating a selection of said object to an application program when said period measured at said step (d) reaches a specific time.

9. A method for operating an object displayed on a screen, comprising the steps of:

(a) excluding a neighborhood of a display area for said object from a movable range for a pointer displayed on a screen;

(b) detecting a movement of said pointer;

(c) determining that said pointer is located in said neighborhood;

(d) changing said display area for said object when it is determined at said step (c) that said pointer is located in said neighborhood; and (e) transmitting an event indicating a selection of said object to an application program when it is determined at said step (c) that said pointer is located in said neighborhood.

10. An apparatus for operating an object displayed on a display screen, comprising:

(a) means for excluding a neighborhood of a display area for said object from a movable range for a pointer displayed on said screen;

(b) means for detecting a movement of said pointer;

(c) means for determining that said pointer is located in said neighborhood, when said movement is detected by said means (b);

(d) means for changing said display area for said object when it is determined by said means (c) that said pointer is located in said neighborhood; and (e) means for transmitting an event indicating a selection of said object to an application program, when it is determined at said step (c) that said pointer is located in said neighborhood.

11. An apparatus, which comprises an LCD device, memory and a CPU in a portable housing case, and which operate an object which is displayed on a screen of said LCD device and located adjacent to one side of a frame of a window on said screen of said LCD device by using a pointer displayed on said screen and controlled by a pointing device, comprising:

(a) means for excluding a neighborhood of a display area for said object from a movable range for said pointer;

(b) means for detecting a movement of said pointer by said pointing device;

(c) means for determining that said pointer is located in said neighborhood when said movement is detected by said means (b);

(d) means for reducing said display area for said object when it is determined by said means (c) that said pointer is located in said neighborhood;

(e) means for enlarging said movable range, according to said display area for said object reduced by said means (d), when said pointer is determined by said means (c) to locate in said neighborhood;

(f) means for repeating operations that are performed by said means (b) through (e);

(g) means for counting a number of repetitions by said means (f);

(h) means for determining when a count by said means (g) reaches a predetermined first value;

(i) means for transmitting an event indicating a selection of said object to an application program when said means (h) determines that said count attains said first value.;

(j) means for performing a process by said application program corresponding to a type of said object;

(k) means for determining that said pointer is located outside of said neighborhood at said means (a); and (l) means for restoring said display area for said object to an original size of said display area of said object at said means (a), when said means (k) determines that said pointer is located outside of said area.

12. The apparatus according to claim 11, wherein a click button is replaced with means (a) through (l).

* * * * *